United States Patent [19]
Bausch

[11] 4,190,177
[45] Feb. 26, 1980

[54] PELLET DISPENSER FOR DENTAL PURPOSE

[76] Inventor: Hans M. Bausch, Monheimer Str. 16, 5000 Koln 60, Fed. Rep. of Germany

[21] Appl. No.: 903,651

[22] Filed: May 8, 1978

[51] Int. Cl.² .................................................. B65D 83/00
[52] U.S. Cl. ............................................ 221/56; 221/61; 206/438
[58] Field of Search .................. 221/34, 45, 46, 52, 221/56–60, 61, 65, 63, 132, 244, 252, 279, 282; 206/438

[56] References Cited
U.S. PATENT DOCUMENTS

| | | | |
|---|---|---|---|
| 1,193,203 | 8/1916 | Taliaferro | 221/132 X |
| 1,365,516 | 1/1921 | Luellen | 221/282 X |
| 2,841,809 | 7/1958 | Oliver | 221/279 X |
| 3,244,318 | 4/1966 | Berryman et al. | 221/63 |
| 3,343,716 | 9/1967 | Peebles | 221/52 X |
| 3,826,406 | 7/1974 | Moniot | 221/52 X |

Primary Examiner—F. J. Bartuska
Attorney, Agent, or Firm—Spensley, Horn, Jubas & Lubitz

[57] ABSTRACT

In this pellet dispenser, foam pellets or the like are made available individually for pickup by the dentist. The dispenser housing includes a cylindrical body with a conical top covered by a cylindrical hood having a conical upper end. The hood has at least one dispensing aperture through which an individual pellet is pressed by the weight of the hood. Advantageously, the conical top includes one or more flat sections so that upon rotation of the hood, the volume available to the pellets will vary as the hood is rotated. This aids in urging pellets into the dispensing apertures.

8 Claims, 4 Drawing Figures

PELLET DISPENSER FOR DENTAL PURPOSE

BACKGROUND OF THE INVENTION

1. Field of the Invention

The present invention relates to a pellet dispenser for dental purposes, and particularly to a dispenser comprising a housing having at least one dispensing aperture and means for pressing individual pellets out of the dispensing aperture.

2. Description of the Prior Art

In dental treatment, a large number of pellets are required to dab or remove blood, saliva or the like from the oral cavity. The pellets typically are wads of cotton or small foam bodies which are seized with an instrument such as pincers or tweezers and applied to the site to be dried. After use, the pellets are thrown away.

It is important that the dentist always have available a sufficient quantity of pellets. The pellets should be supplied individually by the dispenser, so that the dentist easily can pick up a single pellet with his instrument. Preferably the pellets should be offered so that they may be removed from the dispenser with one hand. During treatment, the dentist is constantly trying to keep the dental area dry and free of saliva. If he must pay too much attention to the dispenser operation so as to remove a pellet, the dried area may again fill with saliva or blood.

A pellet dispenser must be so constructed that the dentist, when removing a single pellet by pincers, touches only the corresponding pellet. If several pellets are touched, they may be infected by the pincers. This is why the pellets may not be stored in an open condition, for instance in a cup. Moreover, with open storage, the risk of airborne bacterial infection is great.

Pellet dispensers are known in which a spring biased pressure plate is provided within a casing. The plate presses the pellets against a discharge opening. Such springs cannot be sterilized in a hot air sterilizer, so that it is difficult to make such dispensers sterile. Moreover, the spring is a mechanical element which may cause jamming, and the spring pressure may vary depending on how full is the dispenser.

It is the object of the invention to provide a pellet dispenser of the type disclosed, which permits the safe removal of individual pellets with one hand only, and which is sterilizable as a whole in a simple manner.

SUMMARY OF THE INVENTION

To solve this problem, the invention provides within the housing at least one inclined surface. A press feeding device consists of a weighted cover which rests on the pellets and is movable relative to the inclined surface.

By moving the cover above the inclined surface, the pellets are pressed into the dispensing apertures. If a pellet is removed from the dispensing aperture, the next pellet is pushed into the dispensing aperture by moving the cover above the inclined surface. Moving the cover may be performed easily with one hand.

The cover conveniently has several dispensing apertures which, upon moving the cover with respect to the inclined surface, each fill with a single pellet. Due to the pressure load, the pellets are pushed out by the weight of the cover. With a single movement of the cover, a pellet with project from each dispensing aperture so that a plurality of pellets are available for use before the cover must be moved again.

In a preferred embodiment of the invention, the housing has a substantially cylindrical vertical body and the cover is a hood which loosely overengages the vertical body. The dispenser thus consists of two parts loosely superimposed. The interior of the housing is entirely closed by the cylindrical overhanging hood so that the pellets may leave it only through the dispensing apertures. The weight of the hood is sufficiently high that the pellets inside the casing are compressed together, with individual pellets being pressed through the dispensing apertures. The hood may be of metal or of sterilizable plastic. Since the specific gravity of plastic generally is too low to impart the desired weight to the cover, a plastic cover may have a metal ring to provide the requisite weight.

Advantageously, use is made of foam pellets, e.g. of foamed polyurethane. Such pellets may be thermally sterilized together with the dispenser while they are contained within its housing.

According to another preferred embodiment of the invention, the upper side of the vertical body is substantially conical, and the hood has a substantially conical upper boundary wall containing several dispensing apertures. By turning the cover or hood, the pellets within the housing are moved into alignment with the dispensing apertures through which they are pressed outwardly. Such action may be enhanced by providing the substantially conical upper portion of the vertical body with one or several flat surfaces. With such configuration, the volume available to contain the pellets is changed at different points in the rotation of the hood.

It is also an object of the invention to provide a pellet dispenser which may be moved without the risk of spilling the pellets.

To this end there is provided a rod which projects upwardly from the upper side of the vertical body. The hood has an aperture through which the rod passes. A knob having a diameter greater than that of the passage, is fitted to the rod above the hood. The knob limits the upward movement of the hood with respect to the vertical body. Moreover, it is a handle to carry the pellet dispenser. Preferably, the length of the rod is such that when the hood is lifted up to the knob, the lower edge of the hood still will extend below the lower edge of the substantially conical upper side of the vertical body. As a result, the interior remains closed so that pellets cannot drop out of the housing.

The invention thus simplifies use of the pellet dispenser, and the risk of unintentionally spilling the entire pellet stock, when the hood is lifted inadvertently, is eliminated.

The knob may be secured detachably to the rod. Preferably, the upper end of the rod is threaded to receive a knob provided with a threaded bore. To fill the pellet dispenser, the knob may be unscrewed and the hood may be lifted from the vertical body by movement along the rod.

The entire pellet dispenser including the rod and the knob preferably consists of a thermally sterilizable material. It may be filled in the evening by the dentist and placed in a sterilizing cabinet overnight. In that way, not only the dispenser, but also the pellets contained in it are sterilized. This is especially possible when the pellets are of a suitable foam, e.g. of foamed polyurethane.

The weight of the vertical body should be sufficient to ensure that, when seated on a flat surface, it will not be displaced when the hood is moved. This aids one-handed operation of the pellet dispenser. The pellet dispenser need not be mounted stationarily, yet it may be conveniently placed without running the risk that it will be moved as individual pellets are removed.

To facilitate rotation of the hood, the latter may be provided with a knurled edge.

BRIEF DESCRIPTION OF THE DRAWINGS

A preferred working example of the invention will be explained hereinafter by referring to the figures, wherein.

DESCRIPTION OF THE PREFERRED EMBODIMENT

Figure 4:
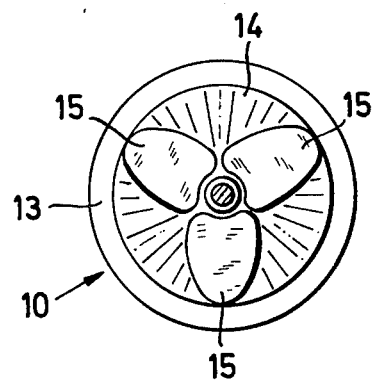
FIG. 4 is a plan view of the vertical body.

The illustrated pellet dispenser comprises a housing consisting of a vertical body 10 and a cover or hood 11 slipped over the vertical body. The vertical body 10 has a cylindrical section 12 whose lower periphery is designed as a collar 13 having a greater diameter. At the top, the cylindrical part is elongated by a cone 14 having three flat sections 15 which extend from the lower cone edge to the flat cone apex. The flat sections 15, as seen in plan view in FIG. 4, are distributed in equal angular distances over the cone surface.

The hood 11 has a cylindrical skirt 16 whose inner diameter is only slightly greater than the outer diameter of the cylindrical section 12 of the vertical body. The hood 11 is open at its lower end and has a conical upper surface 17, the cone angle of which corresponds more or less to that of the cone 14. The conical surface 17 is perforated by a number of dispensing apertures 18. A rod 22 vertically projects upwardly from the flat cone apex of the vertical body 10, and extends through an opening 23 in the apex of the hood 11. At its upper end, it has a knob 24 formed for instance as a ball. The knob 24 has a threaded bore into which the threaded end of rod 24 is screwed. By this means, the knob 24 may be secured screwed onto the rod 22 and it can be unscrewed from the rod by turning in the opposite direction.

In the cylindrical skirt region 16 of the hood, there is provided a roundabout projecting knurled edge 19 to facilitate rotation of the hood.

Figure 1:
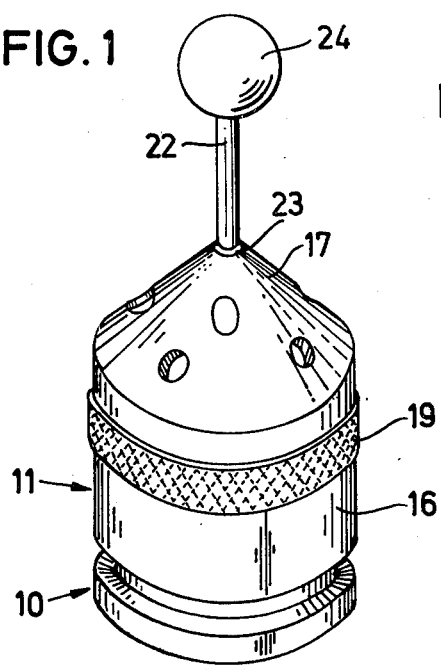
FIG. 1 shows a perspective view of the pellet dispenser.
Figure 2:
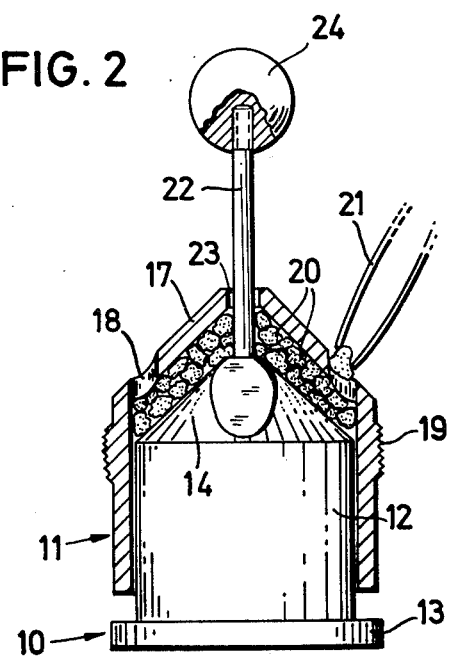
FIG. 2 is a longitudinal section through the pellet dispenser according to FIG. 1.
Figure 3:
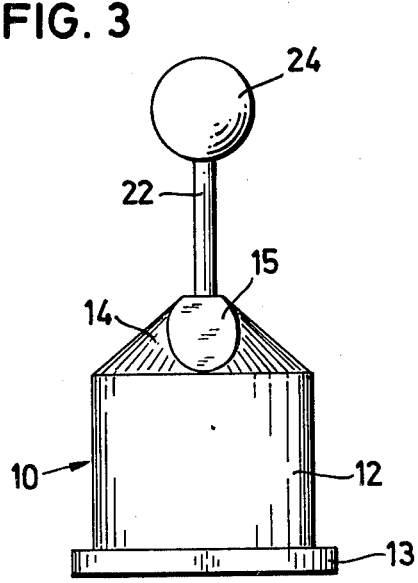
FIG. 3 is a side view.

The pellets 20 disposed inside the space confined by the cone 14 and the conical surface 17 may be of a soft, compressible, absorbent foam material. To fill the housing with pellets, the knob 24 is removed from the rod 22 and the hood 11 is lifted off and held with the apex pointed downward. The pellets are fed into the hood while it is held in this "upside down" orientation. The vertical body 10 then is placed into the hood, as the rod 22 is pushed through the opening 23. Thereafter the two assembled parts are turned right side up and placed on a table or other flat support in the manner shown in FIGS. 1 and 2. The knob 24 is screwed onto the rod, and forms a stop to ensure that the hood 11 can only be lifted so far that the lower edge of the skirt 16 will still overhang the upper portion of the cylindrical part 12. If the hood could be lifted higher, there would be the risk of the pellets dropping out.

After the filled dispenser has been set up, the hood 11 is turned by engaging the knurled edge 19. In addition, a slight pressure may be applied in a downward direction. During the rotation, individual pellets get into the dispensing apertures 18 so that they may be picked up by pincers 21. If none of the dispensing apertures 18 contains an outwardly projecting pellet, the hood 11 is rotated again so that new pellets will get into the dispensing apertures 18.

What is claimed is:

1. A pellet dispenser for dental purposes comprising:
    a housing having at least one dispensing aperture,
    means for pressing individual pellets out of the dispensing aperture, and
    at least one inclined surface inside the housing,
    said pressing means consisting of a cover under weight load which rests on the pellets and is movable relative to the inclined surface,
    said dispenser having a substantially cylindrical vertical body, said cover being designed as a hood loosely overengaging said vertical body, and
    wherein a rod projects upwardly from the top of said vertical body, wherein said hood has an opening for the free passage of the rod, and wherein a knob having a diameter greater than that of said opening is provided on the rod above said hood.

2. A pellet dispenser according to claim 1 wherein the top of said vertical body is substantially conical and wherein said hood also has a conical upper boundary wall in which there are several dispensing apertures.

3. A pellet dispenser according to claim 1 wherein said rod is so long that with the hood lifted up to the knob, the lower edge of the hood still covers the lower edge of the substantially conical top of the vertical body.

4. A pellet dispenser according to claim 1 wherein said knob is detachable from the rod.

5. A pellet dispenser according to claim 1 wherein the top of the vertical body is substantially conical and has several flat surfaces provided in equal angular distances.

6. A pellet dispenser according to claim 1 wherein all parts are of a thermally sterilizable material.

7. A pellet dispenser according to claim 1 wherein the weight of the vertical body is sufficient that the vertical body standing on a level plane will not move upon rotation of the hood.

8. A pellet dispenser for dental purposes comprising:
    a substantially cylindrical vertical body having an inclined upper surface,
    a weighted hood covering said body and being movable relative thereto, said hood having a cylindrical skirt overhanging said cylindrical body and having an inclined lid facing said body upper surface, there being at least one dispensing aperture in said lid, pellets contained between said body inclined upper surface and said hood lid being dispensable individually through said at least one aperture, and
    wherein a rod projects upwardly from the top of said vertical body, wherein said hood has an opening for the free passage of the rod, and wherein a knob having a diameter greater than that of said opening is provided on the rod above said hood.

* * * * *